(12) United States Patent
Ranjan

(10) Patent No.: US 10,080,539 B2
(45) Date of Patent: Sep. 25, 2018

(54) SYSTEMS AND METHODS FOR X-RAY IMAGE PASTING

(71) Applicant: GENERAL ELECTRIC COMPANY, Schenectady, NY (US)

(72) Inventor: Sohan Rashmi Ranjan, Bangalore (IN)

(73) Assignee: General Electric Company, Schenectady, NY (US)

( * ) Notice: Subject to any disclaimer, the term of this patent is extended or adjusted under 35 U.S.C. 154(b) by 37 days.

(21) Appl. No.: 15/334,639

(22) Filed: Oct. 26, 2016

(65) Prior Publication Data
US 2017/0143290 A1 May 25, 2017

(30) Foreign Application Priority Data
Nov. 25, 2015 (IN) .............. 6329/CHE/2015

(51) Int. Cl.
*G06K 9/00* (2006.01)
*A61B 6/00* (2006.01)
(Continued)

(52) U.S. Cl.
CPC .............. *A61B 6/5241* (2013.01); *A61B 6/54* (2013.01); *G06K 9/6215* (2013.01);
(Continued)

(58) Field of Classification Search
CPC ......... A61B 6/5241; A61B 6/54; A61B 18/02; A61B 2017/00482; A61B 2018/0262; A61B 2018/1861; A61B 2034/101; A61B 2034/104; A61B 2090/378; A61B 34/10; G06K 9/6215; G06K 9/6298; G06K 2009/00644; G06K 2009/4657; G06K 9/00127; G06K 9/0014; G06T 11/60; G06T 2207/10116; G06T 2200/32; G06T 2207/10016; G06T 2207/30008; G06T 3/4038; G06T 7/0085; G06T 7/337; G06T 7/13; G06T 11/206; G06T 15/04; G06T 2200/28; G06T 2207/20052;
(Continued)

(56) References Cited

U.S. PATENT DOCUMENTS 5,867,584 A * 2/1999 Hu ................ G06K 9/32
348/169
6,484,048 B1 * 11/2002 Hoshino ............ G01R 33/4833
345/419

(Continued)

*Primary Examiner* — Aklilu Woldemariam
(74) *Attorney, Agent, or Firm* — GE Global Patent Operation; Marc A. Vivenzio

(57) ABSTRACT

A method includes receiving a first image and a second image from an X-ray imaging device and determining a template window in the first image and a plurality of search windows in the second image. The method further includes generating a template vector corresponding to the template window and a plurality of search vectors corresponding to the plurality of search windows. The method also includes calculating a plurality of similarity scores based on the template vector and the plurality of search vectors. Additionally, the method includes determining a matching window from the plurality of search windows based on the plurality of similarity scores. Finally, the method includes generating a final image using the first image and the second image based on the template window and the matching window.

9 Claims, 6 Drawing Sheets

(51) Int. Cl.
*G06T 11/60* (2006.01)
*G06K 9/62* (2006.01)
*G06T 7/33* (2017.01)
*G06T 3/40* (2006.01)

(52) U.S. Cl.
CPC ............ *G06T 3/4038* (2013.01); *G06T 7/337* (2017.01); *G06T 11/60* (2013.01); *G06K 9/00* (2013.01); *G06T 2200/32* (2013.01); *G06T 2207/10016* (2013.01); *G06T 2207/10116* (2013.01); *G06T 2207/20221* (2013.01); *G06T 2207/30008* (2013.01)

(58) Field of Classification Search
CPC ....... G06T 2207/20072; G06T 2207/03; G06T 2200/24; G06T 2207/10056; G06T 2207/30024; G06T 7/0012; G06T 7/248; G06T 7/20; G06T 7/246; G06T 7/277; G06T 2207/30068; G06T 2207/10121; G06T 2207/0072; G06T 2207/20221; G06T 2207/30101; G01R 33/4833; G01R 33/56; C12Q 1/6869; C12Q 2535/122; C12Q 1/6874
USPC .......... 382/107, 132, 224, 202, 199; 606/21, 606/130; 600/104, 109, 424
See application file for complete search history.

(56) References Cited

U.S. PATENT DOCUMENTS

| | | | |
|---|---|---|---|
| 6,999,625 B1* | 2/2006 | Nelson | G06K 9/50 382/103 |
| 2001/0036304 A1* | 11/2001 | Yang | G06K 9/00127 382/132 |
| 2002/0016599 A1* | 2/2002 | Kienzle, III | A61B 17/1703 606/130 |
| 2005/0149360 A1* | 7/2005 | Galperin | G06F 17/30247 705/2 |
| 2008/0095237 A1* | 4/2008 | Hussain | G06T 15/04 375/240.16 |
| 2009/0171203 A1* | 7/2009 | Avital | A61B 18/02 600/439 |
| 2011/0286635 A1* | 11/2011 | Nishigaki | G06T 7/248 382/107 |
| 2013/0101230 A1* | 4/2013 | Holeva | G06T 7/0085 382/202 |
| 2015/0003741 A1* | 1/2015 | Zhang | G06T 7/0085 382/199 |
| 2015/0110245 A1* | 4/2015 | Kim | A61B 6/48 378/62 |
| 2016/0120493 A1* | 5/2016 | Maeda | A61B 6/032 382/131 |
| 2016/0235388 A1* | 8/2016 | Zhang | A61B 6/547 |

* cited by examiner

SYSTEMS AND METHODS FOR X-RAY IMAGE PASTING

CROSS-REFERENCE TO RELATED APPLICATIONS

This application claims foreign priority benefits under 35 U.S.C. 119(a) to Indian Application No. 6329/CHE/2015, filed on Nov. 25, 2015, which is incorporated herein by reference in its entirety.

BACKGROUND

The technology disclosed herein generally relates to X-ray imaging systems. More specifically, the technology disclosed herein relates to systems and methods for pasting a plurality of X-ray images.

Typically, a field of view (FOV) of an X-ray image is constrained by the size of a detector of an X-ray imaging system. Often, healthcare professionals favor viewing, for example, an anatomical area/region of a patient that is larger than the FOV of a single X-ray image. Use of image pasting for generating the final image simulates providing a larger field of view of anatomy than what is possible today by a single digital acquisition. Consequently, multiple X-ray images are acquired. These images are registered and merged together.

Currently available methods to generate the final image from the multiple X-ray images entail pasting of the X-ray images to merge the multiple X-ray images. However, these methods suffer from have numerous problems due to, for example, dose variations in acquiring the X-ray images, motion of the patient while acquiring the X-ray images, presence of implants in the patient, presence of noise in the X-ray images, and the like. As will be appreciated, erroneous registration and pasting of the multiple X-ray images may lead to, for example, erroneous diagnosis and treatment methods of the patient.

Additionally, the efficiency of the pasting process is dependent on accuracy of the registration of the multiple images. By way of example, errors that arise as a consequence of poor registration of images may lead to wrong diagnosis of infection, tumor, or injury. Other examples include error in vertebrae counting, fracture identification, and the like. The unique features of this invention are the elegant solutions for the major failure modes of existing methods described above.

BRIEF DESCRIPTION

In accordance with one aspect of the present specification, a method includes receiving a first X-ray image and a second X-ray image from an X-ray imaging device and determining a template window in the first X-ray image and a plurality of search windows in the X-ray second image. The method further includes generating a template vector corresponding to the template window and a plurality of search vectors corresponding to the plurality of search windows. The method also includes calculating a plurality of similarity scores based on the template vector and the plurality of search vectors. Additionally, the method includes determining a matching window from the plurality of search windows based on the plurality of similarity scores. Finally, the method includes generating a final image using the first X-ray image and the X-ray second image based on the template window and the matching window.

In accordance with one aspect of the present specification, a controller includes a communication subunit configured to receive a first X-ray image and a second X-ray image from an X-ray imaging device. The controller further includes a vector subunit configured to determine a template window in the first X-ray image and a plurality of search windows in the second X-ray image and generate a template vector corresponding to the template window and a plurality of search vectors corresponding to the plurality of search windows. The controller also includes a comparison subunit configured to calculate a plurality of similarity scores based on the template vector and the plurality of search vectors. Additionally, the controller includes a final image subunit configured to determine a matching window from the plurality of search windows based on the plurality of similarity scores and generate a final image using the first X-ray image and the second X-ray image based on the template window and the matching window.

In accordance with one aspect of the present specification, a system includes an X-ray imaging device configured to generate a first X-ray image and a second X-ray image of a subject. The system further includes a controller communicatively coupled with the X-ray imaging device. The controller includes a communication subunit configured to receive a first X-ray image and a second X-ray image from an X-ray imaging device. The controller further includes a vector subunit configured to determine a template window in the first X-ray image and a plurality of search windows in the second X-ray image and generate a template vector corresponding to the template window and a plurality of search vectors corresponding to the plurality of search windows. The controller also includes a comparison subunit configured to calculate a plurality of similarity scores based on the template vector and the plurality of search vectors. Additionally, the controller includes a final image subunit configured to determine a matching window from the plurality of search windows based on the plurality of similarity scores and generate a final image using the first X-ray image and the second X-ray image based on the template window and the matching window.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

In the following specification and the claims, reference will be made to a number of terms, which shall be defined to have the following meanings.

The singular forms "a", "an", and "the" include plural references unless the context clearly dictates otherwise.

As used herein, the term "non-transitory computer-readable media" is intended to be representative of any tangible computer-based device implemented in any method or technology for short-term and/or long-term storage of information, such as, computer-readable instructions, data structures, program modules and sub-modules, or other data in any device. Therefore, methods described herein may be encoded as executable instructions embodied in a tangible, non-transitory, computer readable medium, including, without limitation, a storage device and/or a memory device. Such instructions, when executed by a processor, cause the processor to perform at least a portion of the methods described herein. Moreover, as used herein, the term "non-transitory computer-readable media" includes all tangible, computer-readable media, including, without limitation, non-transitory computer storage devices, including, without limitation, volatile and non-volatile media, and removable and non-removable media such as a firmware, physical and virtual storage, a compact disc read only memory, a digital versatile disc, and any other digital source such as a network or the Internet, as well as yet to be developed digital means, with the sole exception being a transitory, propagating signal.

Further, as used herein, the terms "software" and "firmware" are interchangeable, and include any computer program stored in memory for execution by devices that include, without limitation, mobile devices, clusters, personal computers, workstations, clients, and servers.

Moreover, as used herein, the term "computer" and related terms, e.g., "computing device", are not limited to integrated circuits referred to in the art as a computer, but broadly refers to at least one microcontroller, microcomputer, programmable logic controller (PLC), application specific integrated circuit, and other programmable circuits, and these terms are used interchangeably herein throughout the specification.

Approximating language, as used herein throughout the specification and claims, may be applied to modify any quantitative representation that could permissibly vary without resulting in a change in the basic function to which it is related. Accordingly, a value modified by a term or terms, such as "about" and "substantially," are not to be limited to the precise value specified. In at least some instances, the approximating language may correspond to the precision of an instrument for measuring the value. Here and throughout the specification and claims, range limitations may be combined and/or interchanged, such ranges are identified and include all the sub-ranges contained therein unless context or language indicates otherwise.

Figure 1:
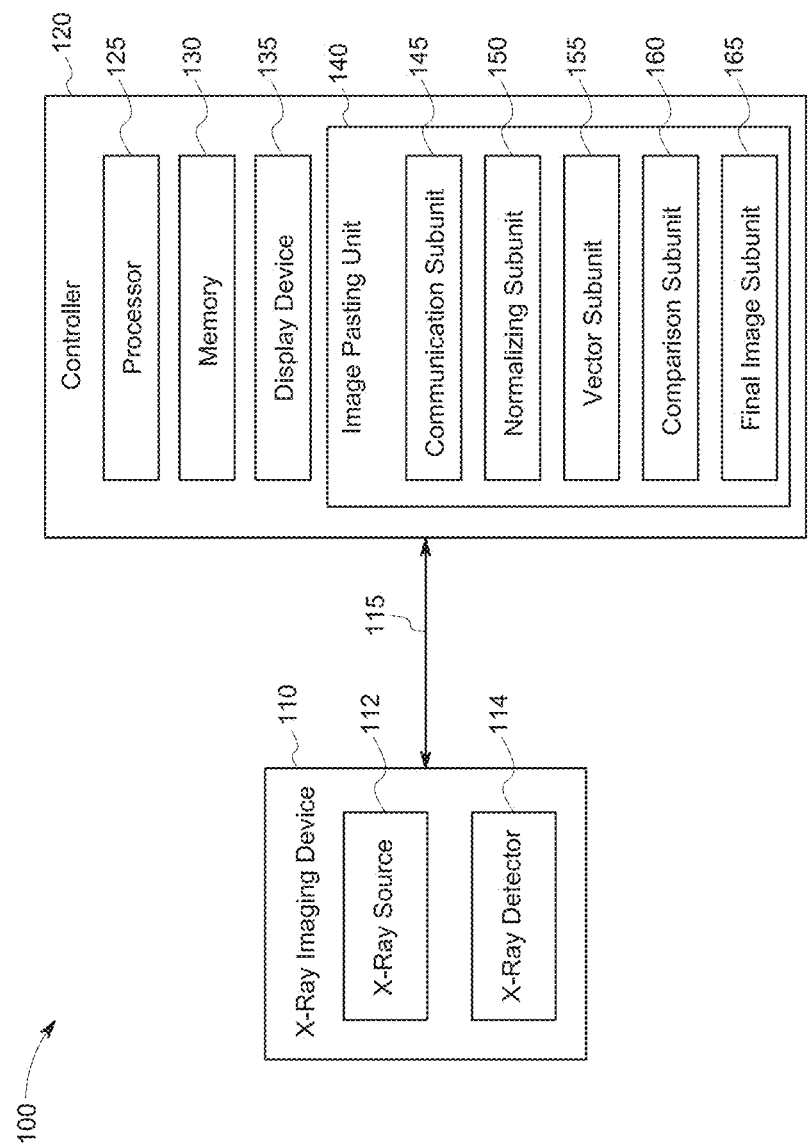
FIG. 1 is a block diagram illustrating an exemplary system for X-ray image pasting in accordance with aspects of the present specification.

Systems and methods for X-ray image pasting are described herein. FIG. 1 illustrates a block diagram of an exemplary system 100 for X-ray image pasting, in accordance with aspects of the present specification. The system 100 includes an X-ray imaging device 110 and a controller 120 that are communicatively coupled to each other. In the illustrated embodiment, the X-ray imaging device 110 and the controller 120 are shown as being communicatively coupled via a wired signal line 115. However, in other embodiments, the X-ray imaging device 110 and the controller 120 may be communicatively coupled wirelessly. Although in the illustrated embodiment, the X-ray imaging device 110 and the controller 120 are depicted as two standalone units, in another embodiment the controller 120 may be included within the X-ray imaging device 110.

The X-ray imaging device 110 may be any type of device configured to generate one or more X-ray images of a subject, for example, a human patient, an animal, an object, and the like. Non-limiting examples of the X-ray imaging device 110 include a digital radiography device, a mammography device, and a dual energy X-ray device.

In the illustrated embodiment, the X-ray imaging device 110 includes an X-ray source 112 configured to project one or more sets of X-rays towards the subject at one or more sets of exposure parameters. The X-ray imaging device 110 further includes an X-ray detector 114 configured to receive the one or more sets of X-rays that are attenuated by the subject and generate one or more X-ray images. A set of exposure parameters may include, for example, a peak kilovoltage (kVp) of the X-ray source 112, an X-ray dose of the X-ray source 112 expressed in milliampere seconds (mAs), a detector position of the X-ray detector 114, a focal spot size, an X-ray exposure time, a sensitivity, and the like. Typically, the one or more sets of exposure parameters are defined either manually by an operator of the X-ray imaging device 110 or automatically by a computing device such as the controller 120.

In one example, the controller 120 may determine the one or more exposure parameters using automatic exposure control methods. The X-ray imaging device 110 is further configured to transmit the one or more X-ray images of the subject to the controller 120 via the signal line 115. In one embodiment, the X-ray imaging device 110 may transmit the one or more X-ray images to the controller 120 in, for example, a Digital Imaging and Communication in Medicine (DICOM) format that includes the corresponding sets of exposure parameters.

Moreover, in one embodiment, the X-ray source 112 is configured to project a first set of X-rays towards a first region (e.g., a head-neck region) of a human patient at a first set of exposure parameters. The first set of exposure parameters includes a first mAs (i.e., a first X-ray dose), a first detector position of the X-ray detector 114, and the like. The X-ray source 112 is also configured to project a second set of X-rays towards a second region (e.g., a chest region) of the human patient at a second set of exposure parameters. The second set of exposure parameters includes a second mAs (i.e., a second X-ray dose), a second detector position of the X-ray detector 114, and the like. Further, the X-ray detector 114 is configured to generate a first X-ray image based on a first set of X-rays attenuated by the first region and a second X-ray image based on a second set of X-rays attenuated by the second region. The X-ray detector 114 is further configured to transmit the first X-ray image and the second X-ray image to the controller 120. In such an embodiment, the X-ray doses such as the first mAs and the second mAs may be different due to the anatomical variations between the first region and the second region of the human patient. Similarly, the first and second detector positions may be different in order to receive the X-rays attenuated by the first and second regions respectively. However, the first detector position of the X-ray detector 114 may partially overlap with the second detector position of the X-ray detector 114. Thus, the first region of the subject in the first X-ray image may partially overlap with the second region of the subject in the X-ray second image.

Furthermore, the controller 120 may be any type of device that is configured to generate a final image of the subject by pasting the one or more X-ray images. While the focus of the discussion herein is on X-ray image pasting, it is noted that the controller 120 may also perform other control features such as, but not limited to, determining a set of exposure parameters, moving the X-ray source 112 and/or the X-ray detector 114, and the like.

In the illustrated embodiment, the controller 120 includes a processor 125, a memory 130, a display device 135, and an image pasting unit 140.

The processor 125 may include at least one arithmetic logic unit, microprocessor, general purpose controller or other processor arrays configured to perform computations, and/or retrieve data stored in the memory 130. In one embodiment, the processor 125 may be a multiple core processor. The processor 125 processes data signals and may include various computing architectures including a complex instruction set computer (CISC) architecture, a reduced instruction set computer (RISC) architecture, or an architecture implementing a combination of instruction sets. In one embodiment, the processing capability of the processor 125 may support the retrieval of data and transmission of data. In another embodiment, the processing capability of the processor 125 may also perform more complex tasks, including various types of feature extraction, modulating, encoding, multiplexing, and the like. Other type of processors, operating systems, and physical configurations are also envisioned.

The memory 130 may be a non-transitory storage medium. For example, the memory 130 may be a dynamic random access memory (DRAM) device, a static random access memory (SRAM) device, flash memory or other memory devices. The memory 130 may also include a non-volatile memory or similar permanent storage device, and media such as a hard disk drive, a floppy disk drive, a compact disc read only memory (CD-ROM) device, a digital versatile disc read only memory (DVD-ROM) device, a digital versatile disc random access memory (DVD-RAM) device, a digital versatile disc rewritable (DVD-RW) device, a flash memory device, or other non-volatile storage devices.

The memory 130 stores data that is required for the image pasting unit 140 to perform associated functions. In one embodiment, the memory 130 stores codes and routines associated with one or more subunits (e.g., a communication subunit 145, a comparison subunit 160, and the like) of the image pasting unit 140. In another embodiment, the memory 130 stores an intensity threshold, a gradient threshold, and a Hessian threshold that are defined by, for example, an administrator of the controller 120 based on previously generated clinical data. The thresholds will be described in further detail with reference to a vector subunit 155 of the image pasting unit 140.

The image pasting unit 140 is configured to receive one or more X-ray images of the subject and generate a final image of the subject by pasting the one or more X-ray images. In the illustrated embodiment, the image pasting unit 140 includes a communication subunit 145, a normalizing subunit 150, a vector subunit 155, a comparison subunit 160, and a final image subunit 165. The plurality of subunits of the image pasting unit 140, the processor 125, the memory 130, and the display device 135 may be coupled to a bus (not shown) for communication with each other. It may be noted that the one or more subunits may include codes and routines that may be implemented as software, hardware, or a combination of software and hardware.

The communication subunit 145 is configured to handle communications between the X-ray imaging device 110, the display device 135, and the one or more subunits of the image pasting unit 140. In one embodiment, the communication subunit 145 includes a set of instructions executable by the processor 125 to provide the functionality for handling communications between the X-ray imaging device 110, the display device 135, and the one or more subunits of the image pasting unit 140. In another embodiment, the communication subunit 145 may be stored in the memory 130 and is accessible and executable by the processor 125. In either embodiment, the communication subunit 145 is adapted for communication and cooperation with the processor 125 and the one or more subunits of the image pasting unit 140.

In one embodiment, the communication subunit 145 receives the first and second X-ray images of the subject from the X-ray imaging device 110. The communication subunit 145 transmits the first and second X-ray images to the normalizing subunit 150. In another embodiment, the communication subunit 145 receives graphical data for providing a final image of the subject to, for example, a clinician. In such an embodiment, the communication subunit 215 transmits the graphical data to the display device 135. Although, the image pasting unit 140 is described herein as receiving two X-ray images and generating the final image by pasting the two X-ray images, in other embodiments the controller 140 may receive more than two X-ray images and generate the final image by pasting the X-ray images.

The normalizing subunit 150 is configured to normalize at least one of the first X-ray image and the second X-ray image. In one embodiment, the normalizing subunit 150 includes a set of instructions executable by the processor 125 to provide the functionality for normalizing at least one of the first X-ray image and the second X-ray image. In another embodiment, the normalizing subunit 150 is stored in the memory 130 and is accessible and executable by the processor 125. In either embodiment, the normalizing subunit 150 is adapted for communication and cooperation with the processor 125 and the one or more subunits of the image pasting unit 140.

Moreover, in one embodiment, the normalizing subunit 150 receives the first and second X-ray images from the communication subunit 145. The first and second X-ray images may be DICOM images that include the first and the second sets of exposure parameters respectively. The normalizing subunit 150 is configured to extract the first and second doses from the first and second sets of exposure parameters and determine a dose ratio based on the first and second doses. Further, the normalizing subunit 150 is configured to normalize at least one of the first and second X-ray images based on the dose ratio. In one embodiment, the normalizing subunit 150 normalizes the first or the second X-ray images by multiplying the first or the second X-ray images with the dose ratio. In another embodiment, the normalizing subunit 150 determines the lower dose amongst the first and second doses. In such an embodiment, if the first dose is lower than the second dose, the normalizing subunit 150 normalizes the first X-ray image based on the dose ratio. However, if the second dose is lower than the first dose, the normalizing subunit 150 normalizes the second X-ray image based on the dose ratio. Although, the normalizing subunit 150 is described as normalizing at least one of the first and second X-ray images based on the ratio according to one embodiment, in other embodiments the normalizing subunit 150 may normalize at least one of the first and second X-ray images based on any of the first and second set of exposure parameters.

In one embodiment, prior to normalizing at least one of the first and second X-ray images, the normalizing subunit 150 is configured to de-noise the first and second X-ray images. For example, the normalizing subunit 150 removes the Poissonian noise from the first and second X-ray images. In such an example, the normalizing subunit 150 may convert the Poissonian noise to unit variance Gaussian noise based on an Ascombe transform. The normalizing subunit 150 may then generate the noise free X-ray images by removing the Gaussian noise and using an inverse Ascombe transform.

Additionally, in certain embodiments, the normalizing subunit 150 is further configured to filter the first and second X-ray images based on a Difference of Gaussian (DoG) filter. Processing the first and second X-ray images based on the DoG filter enhances the edge content (e.g., edges of bone) and aids in registering and pasting the first and second X-ray images. For the purpose of clarity and convenience, the first X-ray image and the second X-ray image that have been, at least one of normalized, de-noised, and filtered by the normalizing subunit 150 are herein referred to as the first image and the second image respectively. The normalizing subunit 150 is further configured to transmit the first and second images to the vector subunit 155 and the final image subunit 165.

The vector subunit 155 is configured to generate a template vector and a plurality of search vectors based on the first image and the second image respectively. In one embodiment, the vector subunit 155 includes a set of instructions executable by the processor 125 to provide the functionality for generating the template vector and the plurality of search vectors based on the first image and the second image respectively. In another embodiment, the vector subunit 155 is stored in the memory 130 and is accessible and executable by the processor 125. In either embodiment, the vector subunit 155 is adapted for communication and cooperation with the processor 125 and the one or more subunits of the image pasting unit 140.

In certain embodiments, the vector subunit 155 receives the first and second images from the normalizing subunit 150. The vector subunit 155 is configured to extract the first and second detector positions from the first and second sets of exposure parameters associated with the first and second images respectively. The vector subunit 155 then determines a region of the subject in the first image that overlaps with the second image (i.e., a region commonly present in the first and second images) based on the first and second detector positions. For the purpose of clarity and convenience, the overlapping region in the first image is herein referred to as a template overlap region. Similarly, for the purpose of clarity and convenience, the overlapping region in the second image is herein referred to as a search overlap region.

Further, the vector subunit 155 is configured to determine a template window (i.e., a plurality of pixels) in the template overlap region. In one example, the vector subunit 155 calculates an edge content of the template overlap region. In such an example, the vector subunit 155 determines a window in the template overlap region that has the highest edge content (i.e., the highest number of edges) in the template window. The size of the template window (e.g., 4×4 pixels, 6×7 pixels, and the like) may be defined by, for example, an administrator of the controller 120 based on previously generated clinical data. Furthermore, the vector subunit 155 is configured to identify a template interest pixel in the template window based on one or more image features of the template window. Non-limiting examples of the one or more image features include an intensity value of each pixel in the template window, a gradient of each pixel in the template window, and a Hessian response of each pixel in the template window. In one example, the vector subunit 155 identifies the pixel with the highest gradient within the template window as the template interest pixel. The vector subunit 155 is also configured to generate a template vector corresponding to the template window based on the template interest pixel and a plurality of pixels surrounding the template interest pixel.

The vector subunit 155 is also configured to determine a plurality of search windows in the search overlap region. In one example, the vector subunit 155 determines the plurality of search windows by determining a search window for each pixel in the search overlap region. Typically, the size of the search window is the same as the size of the template window. Further, the vector subunit 155 is configured to identify a search interest pixel for each of the plurality of search windows based on a location of the template interest pixel within the template window. In one example, if the vector subunit 155 identifies a pixel with a two-dimensional (2D) location (2, 2) as the template interest pixel in a template window with a size of 4×4 pixels, the vector subunit 155 identifies a pixel with a 2D location (2, 2) in each of the plurality of search windows as the search interest pixel. The vector subunit 155 is further configured to generate a search vector corresponding to each of the plurality of search windows based on the plurality of search interest pixels and a plurality of pixels surrounding each of the plurality of search interest pixels.

In one embodiment, the vector subunit 155 may receive an irrelevant mask indicating one or more irrelevant pixels in the first and second images that represent one or more irrelevant objects in the first and second images. Non-limiting examples of an irrelevant object include a metal implant in the subject, jewelry worn by a subject at the time of imaging, noise, and the like. In one example, the irrelevant mask may be defined by an administrator of the controller 120. In another example, the vector subunit 155 may receive the irrelevant mask from a segmentation unit (not shown) coupled with the controller 120 and configured to segment the one or more irrelevant objects from the first and second images. In such an embodiment, the vector subunit 155 is configured to generate the template vector based on the template interest pixel, the one or more pixels surrounding the template interest pixel, and the irrelevant mask. Similarly, the vector subunit 155 is configured to generate the plurality of search vectors based on the plurality of search pixels, the one or more pixels surrounding each of the plurality of search interest pixels, and the irrelevant mask. The template window, the plurality of search windows, the template vector, and the plurality of search vectors will be described in greater detail with reference to FIGS. 2 and 3. Further, the vector subunit 155 is configured to transmit the template vector and the plurality of search vectors to the comparison subunit 160.

Although, the vector subunit 155 is described herein as determining a single template interest pixel, in other embodiments the vector subunit 155 may determine a plurality of template interest pixels in the template window. In one example, if the vector subunit 155 determines that the Hessian response of two pixels in the template window exceeds a Hessian threshold, the vector subunit 155 identifies two pixels as a first and second template interest pixels.

Similarly, the vector subunit 155 may also identify two pixels as template interest pixels if their intensity values and/or their gradients exceed an intensity and/or gradient threshold respectively. As noted previously, the Hessian threshold, intensity threshold, and gradient threshold may be defined by, for example, an administrator of the controller 120 based on previously generated clinical data. In such an example, the vector subunit 155 further generates the template vector based on the first and second template interest pixels and the one or more pixels surrounding the first and second template interest pixels. Furthermore, the vector subunit 155 determines a first and a second search interest pixel for each of the plurality of search windows. Additionally, the vector subunit 155 generates a plurality of search vectors based on the intensity values of the first and second search interest pixels and one or more pixels surrounding the first and second interest pixels in each of the plurality of search windows.

The comparison subunit 160 is configured to calculate a plurality of similarity scores by comparing the template vector with each of the plurality of search vectors. In one embodiment, the comparison subunit 160 includes a set of instructions executable by the processor 125 to provide the functionality for calculating a plurality of similarity scores by comparing the template vector with each of the plurality of search vectors. In another embodiment, the comparison subunit 160 is stored in the memory 130 and is accessible and executable by the processor 125. In either embodiment, the comparison subunit 160 is adapted for communication and cooperation with the processor 125 and the one or more subunits of the image pasting unit 140.

In one embodiment, the comparison subunit 160 receives the template vector corresponding to the template window and the plurality of search vectors corresponding to the plurality of search windows from the vector subunit 155. The comparison subunit 160 generates a similarity score for each search window by comparing the template vector with the corresponding search vector. In one example, the comparison subunit 160 computes a distance (e.g., a hamming distance) between the template vector and a search vector. The comparison subunit 160 then generates the similarity score for the search window based on the distance. Typically, a similarity score of a search window is inversely proportional to the distance between the template vector and the corresponding search vector. In another example, comparison unit 160 generates a similarity score for a search window based on equation (1).

$$\text{Similarity Score} = \text{match number} - \text{mismatch number} \quad (1)$$

In equation (1), the match number represents a number of matches between elements of the template vector and the search vector and the mismatch number is indicative of a number of mismatches between the elements of the template vector and the search vector. In either example, the comparison subunit 160 is further configured to transmit the plurality of similarity scores corresponding to the plurality of search windows to the final image subunit 165.

The final image subunit 165 is configured to generate a final image of the subject. In one embodiment, the final image subunit 165 includes a set of instructions executable by the processor 125 to provide the functionality for generating the final image of the subject. In another embodiment, the final image subunit 165 is stored in the memory 130 and is accessible and executable by the processor 125. In either embodiment, the final image subunit 165 is adapted for communication and cooperation with the processor 125 and the one or more subunits of the image pasting unit 140.

In one embodiment, the final image subunit 165 receives the first and second images from the normalizing subunit 150. Additionally, the final image subunit 165 receives the plurality of similarity scores corresponding to the plurality of search windows in the second image from the comparison subunit 160. The final image subunit 165 is configured to determine a matching window in the second image that corresponds to the template window in the first image based on the plurality of similarity scores. In one example, the final image subunit 165 may identify the search window with the highest similarity score as the matching window. In another example, the final image subunit 165 may identify a plurality of search windows that have the highest similarity score. In such an example, the final image subunit 165 identifies a matching window from the plurality of search windows based on, for example, a z-score analysis, mutual information score analysis, and the like. Further, the final image subunit 165 is configured to generate a shift vector and register the first and the second images based on the 2D locations of the template window and the matching window. Furthermore, the final image subunit 165 is configured to generate the final image of the subject by pasting the first image and the second image based on the 2D locations of the template window and the matching window.

Additionally, the final image subunit 165 may be further configured to generate graphical data for providing the final image to, for example, a clinician, an operator of the X-ray imaging device 110, and the like, for diagnosis of the subject. In one embodiment, the final image subunit 165 transmits the graphical data for providing the final image to a display device 135. In such an embodiment, the display device 135 renders the graphical data and displays the final image to, for example, an operator of the X-ray imaging device 110. In another embodiment, the final image subunit 165 sends the graphical data for providing the final image to an operator of the X-ray imaging device 110, a clinician, and the like, via, for example, an electronic mail, short messaging service, and the like.

Figure 2:
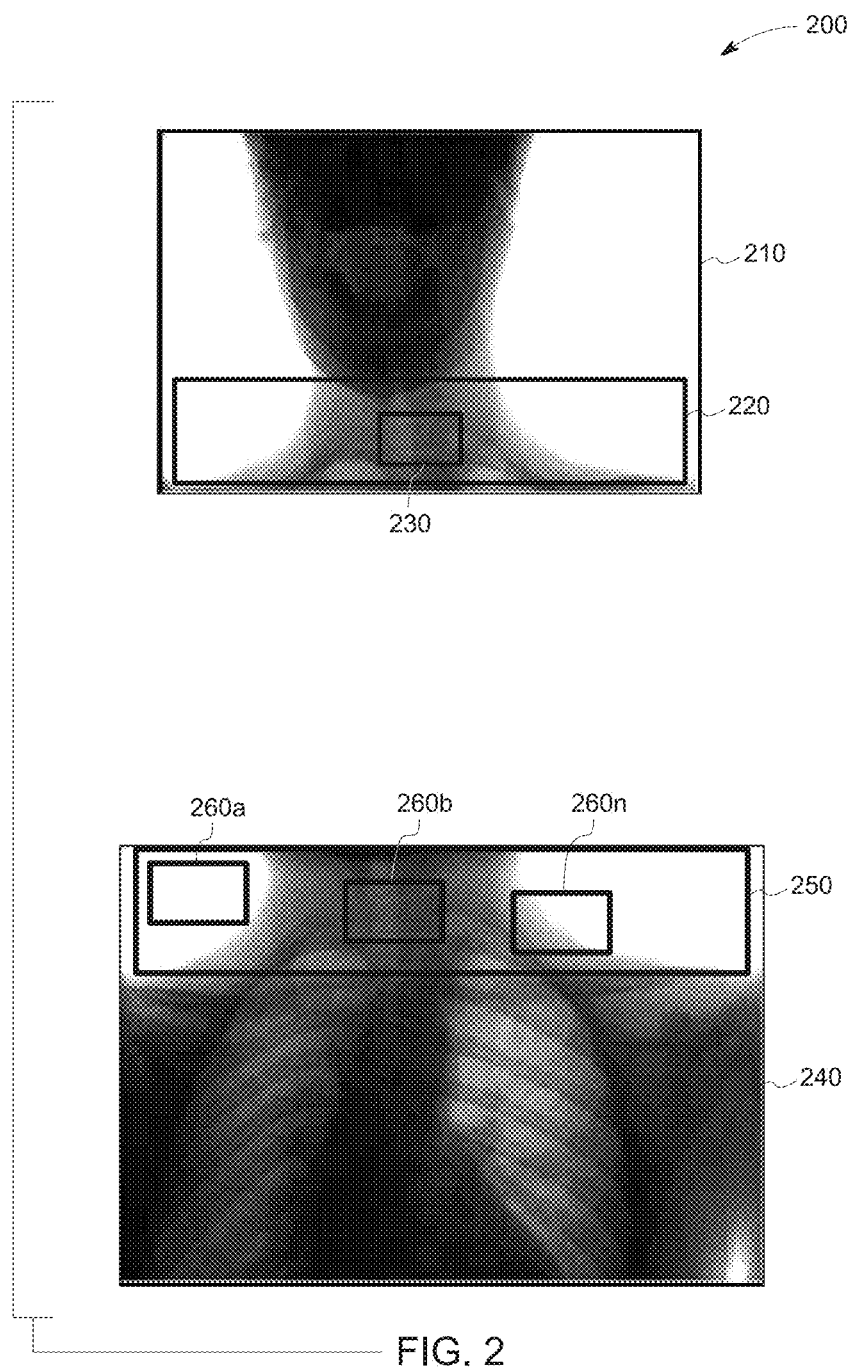
FIG. 2 depicts pictorial representations of a method of determining a template window and a plurality of search windows in a plurality of X-ray images, in accordance with aspects of the present specification.

Referring now to FIG. 2, pictorial representation 200, 235 of a first image 210 and a second image 240 are illustrated, in accordance with aspects of the present specification. For ease of explanation, FIG. 2 is described with reference to the elements of FIG. 1.

The image pasting unit 140 receives the first image 210 and the second image 240 from the X-ray imaging device 110. The vector subunit 155 determines a template overlap region 220 in the first image 210 based on a first detector position of the X-ray detector 114 of the X-ray imaging device 110. Similarly, the vector subunit 155 determines a search overlap region 250 in the second image 240 based on a second detector position of the X-ray detector 114 of the X-ray imaging device 110. Further, the vector subunit 155 determines a template window 230 based on edge content of the template overlap region 220. Additionally, the vector subunit 155 determines a plurality of search windows 260a, 260b, . . . , 260n based on a plurality of pixels in the search overlap region 250. As noted previously, the size of the template window 230 and the plurality of search windows 260a, 260b, . . . , 260n may be determined by, for example, an administrator of the controller 120.

Figure 3:
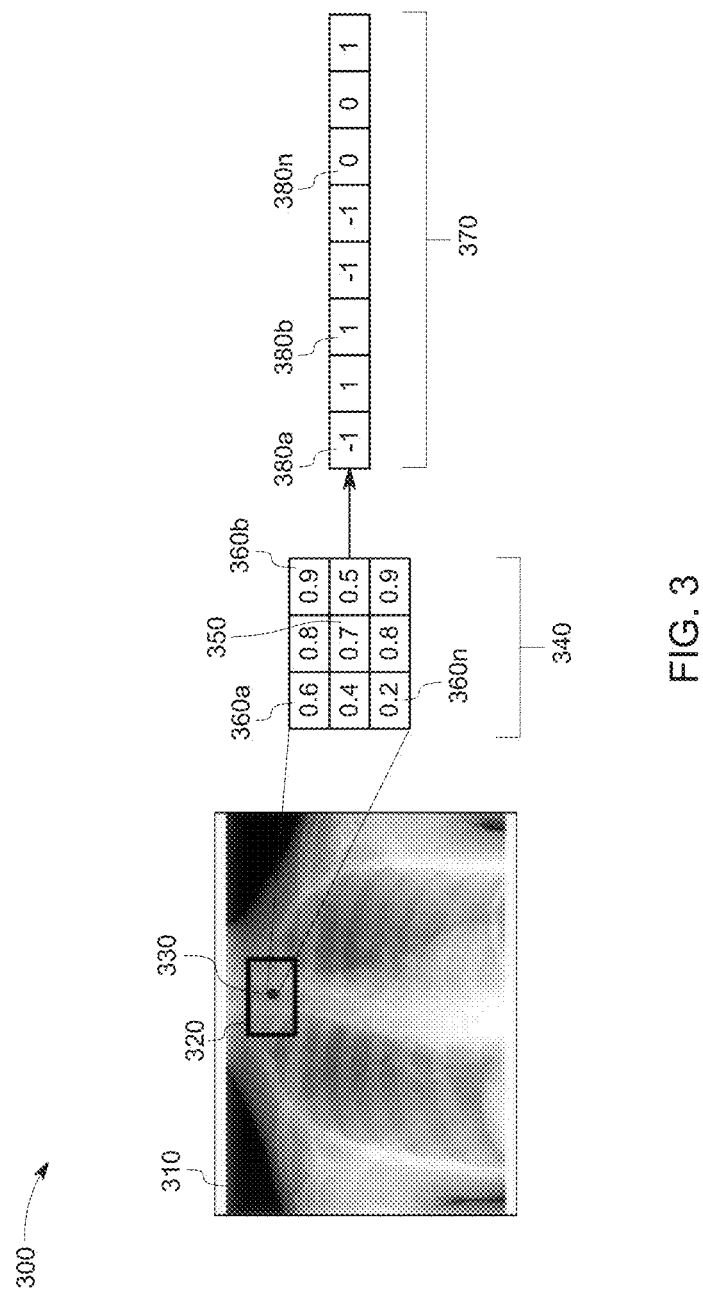
FIG. 3 is a schematic representation of an exemplary method for generating a template vector, in accordance with aspects of the present specification.

FIG. 3 is a schematic representation 300 of an exemplary method for generating a template vector 370, in accordance with aspects of the present specification. The method of generating the template vector 370 of FIG. 3 will be described with reference to the components of FIG. 1. In the illustrated embodiment, the vector subunit 155 receives a first image 310 and determines a template window 320. The vector subunit 155 further identifies a template interest pixel 330 within the template window 320 based on, for example, gradients of the pixels within the template window 320. Reference numeral 340 represents a matrix 340 that is indicative of an intensity value 350 of the template interest pixel 330 and intensity values 360a, 360b, . . . , 360n of a plurality of pixels that surround the template interest pixel 350.

In the embodiment of FIG. 3, the vector subunit 155 further receives an irrelevant mask that is indicative of one or more irrelevant pixels in the first image 310. The vector subunit 155 generates the template vector 370 based on the intensity value 350 of template interest pixel 330, the intensity values 360a, 360b, . . . , 360n of the plurality of pixels that surround the template interest pixel 330, and the irrelevant mask. In one example, the vector subunit 155 generates the template vector 370 based on equation (2).

$$V_i = \begin{cases} 0, & \text{if } S_i \text{ is irrelevant} \\ 1, & \text{if } S_i \geq T \\ -1, & \text{otherwise} \end{cases} \quad (2)$$

where, V represents the template vector, S represents the intensity values of the pixels surrounding the template interest pixel, T represents the intensity value of the template interest pixel, and i=1, 2, . . . , n, where n is the number of pixels surrounding the template interest pixel.

Furthermore, the vector subunit 155 computes one or more elements 380a, 380b, . . . , 380n of the template vector 370 based on a comparison of the intensity values 360a, 360b, . . . , 360n of the surrounding pixels with the intensity value 350 of the template interest pixel 330. By way of example, the vector subunit 155 computes an element 380a of the template vector 370 as −1, since the intensity value 360a is lower than the intensity value 350 of the template interest pixel 330. Similarly, the vector subunit 155 also computes an element 380b of the template vector 370 as +1, since the intensity value 360b is higher than the intensity value 350 of the template interest pixel 330. The vector subunit 155 computes the element 380n as 0, since the irrelevant mask indicates that the intensity value 360n is irrelevant. As noted above, the vector subunit 155 may further generate a search vector for a search window based on a search interest pixel, intensity values of a plurality of pixels surrounding the search interest pixel, and a neighborhood mask using equation (2).

Figure 4:
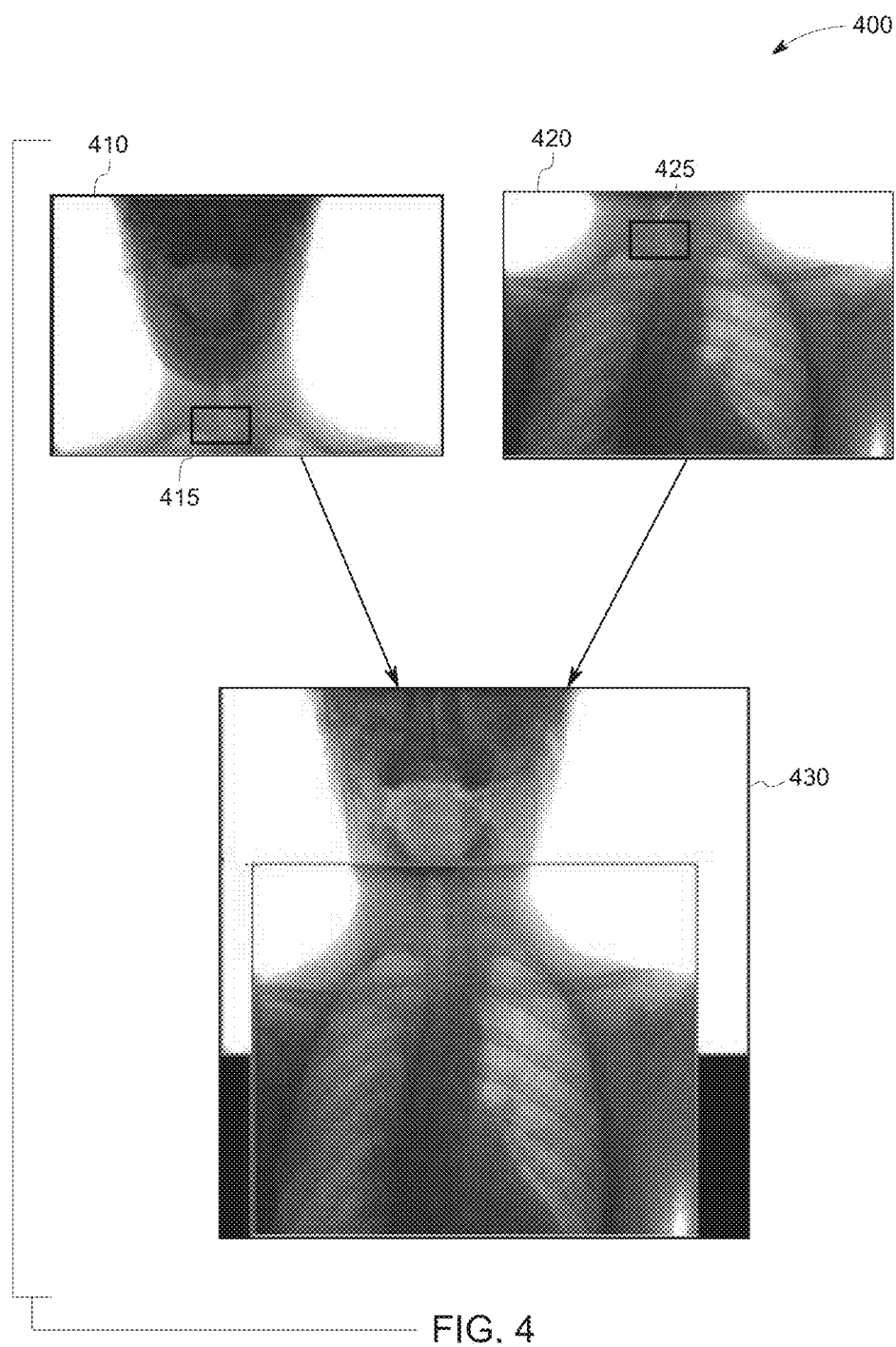
FIG. 4 is a schematic representation of an exemplary method for pasting a plurality of X-ray images, in accordance with aspects of the present specification.

Referring now to FIG. 4, a schematic representation of an exemplary method 400 for generating a final image 430, in accordance with aspects of the present specification, is illustrated. For ease of explanation, the method of generating the final image 430 of FIG. 4 will be described with reference to the components of FIG. 1. In the illustrated embodiment, the final image subunit 165 receives a first image 410 and a second image 420 of a subject. As previously noted with reference to FIG. 1, in certain embodiments, the final image subunit 165 generates the final image of the subject by pasting first and second images together based on a template window in the first image and a matching window in the second image. Accordingly, in the example of FIG. 4, the final image subunit 165 generates the final image 430 of the subject by pasting the first and second images 410, 420 together based on a template window 415 in the first image 410 and a matching window 425 in the second image 420.

Figure 5:
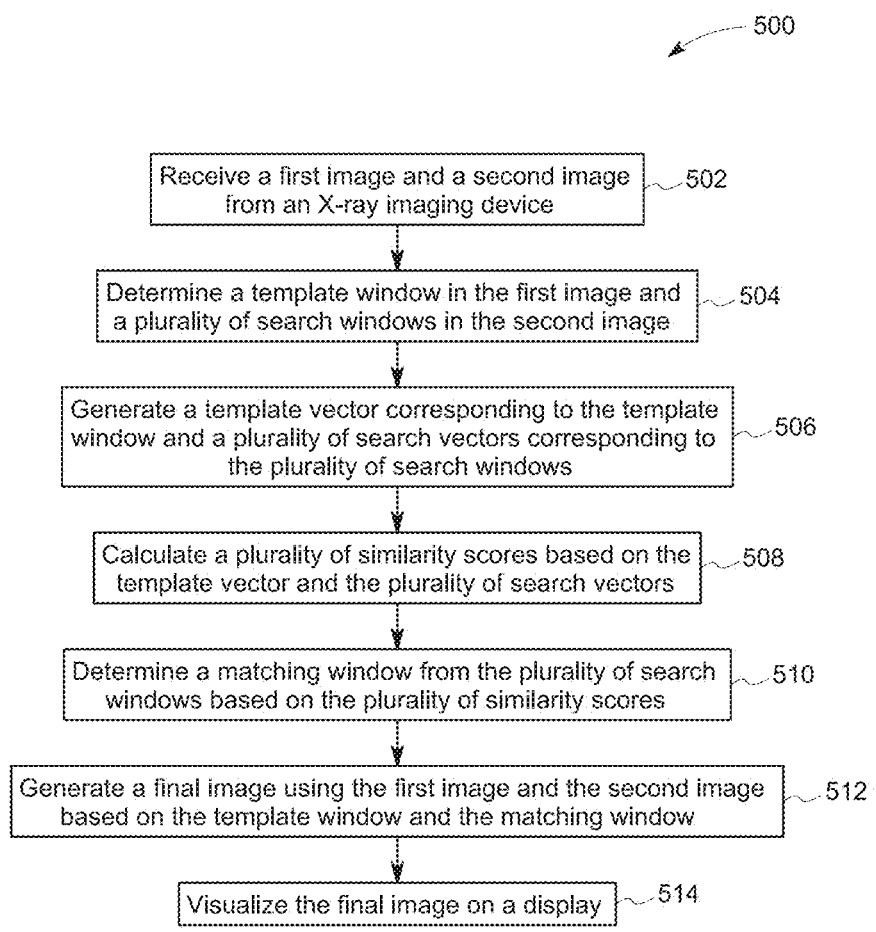
FIG. 5 is a flow chart illustrating an exemplary method for pasting a plurality of X-ray images, in accordance with aspects of the present specification.

FIG. 5 is a flow chart illustrating an exemplary method 500 for pasting a plurality of images, in accordance with aspects of the present specification. The method of FIG. 5 is described with reference to components of FIG. 1.

At step 502, the communication subunit 145 receives a first image and a second image from the X-ray imaging device 110. Further, at step 504, the vector subunit 155 determines a template window in the first image and a plurality of search windows in the second image. Moreover, at step 506, the vector subunit 155 generates a template vector corresponding to the template window and a plurality of search vectors corresponding to the plurality of search windows. For example, the vector subunit 155 generates the template vector and the plurality of search vectors based on equation (2). Also, at step 508, the comparison subunit 160 calculates a plurality of similarity scores based on the template vector and the plurality of search vectors. For example, the comparison subunit 160 calculates the plurality of similarity scores between the template vector and each of the plurality of search vectors based on equation (1).

Additionally, at step 510, the final image subunit 165 determines a matching window from the plurality of search windows based on the plurality of similarity scores. For example, the final image subunit 165 identifies a search window with the highest similarity score as the matching window. Also, as indicated by step 512, the final image subunit 165 generates a final image using the first image and the second image based on the template window and the matching window. For example, the final image subunit 165 pastes the first and second images together based on a location of the template window in the first image and a location of the matching window in the second image. Subsequently, at step 514, the final image is visualized on a display device 135. For example, the final image subunit 165 may generate and transmit graphical data of the final image to a display device 135. The visualization may aid, for example, a clinician to diagnose a subject based on the final image.

Figure 6:
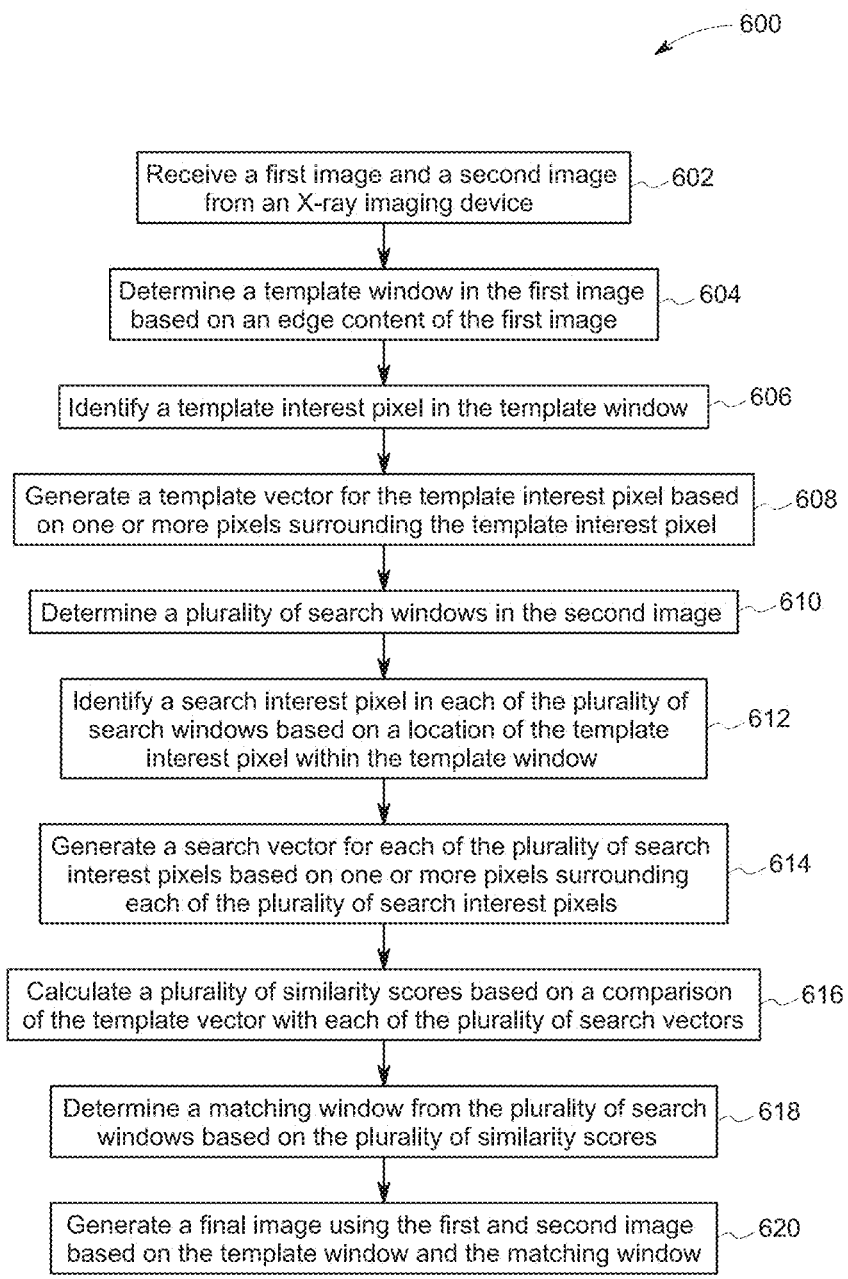
FIG. 6 is a flow chart illustrating another exemplary method for pasting a plurality of X-ray images, in accordance with aspects of the present specification.

Turning now to FIG. 6, a flow chart illustrating another exemplary method 600 for pasting a plurality of images, in accordance with aspects of the present specification, is depicted. The method of FIG. 6 is described with reference to components of FIG. 1.

At step 602, the communication subunit 145 receives a first image and a second image from the X-ray imaging device 110. At step 604, the vector subunit 155 determines a template window in the first image based on edge content of the first image. Additionally, at step 606, the vector subunit 155 identifies a template interest pixel in the template window. Subsequently, at step 608, the vector subunit 155 generates a template vector for the template interest pixel based on one or more pixels surrounding the template interest pixel.

Further, at step 610, the vector subunit 155 determines a plurality of search windows in the second image. Furthermore, at step 612, the vector subunit 155 identifies a search interest pixel in each of the plurality of search windows based on a location of the template interest pixel within the template window. Also, as indicated by step 614, the vector subunit 155 generates a search vector for each of the plurality of search interest pixels based on one or more pixels surrounding each of the plurality of search interest pixels. Moreover, at step 616, the comparison subunit 160 calculates a plurality of similarity scores based on a comparison of the template vector with each of the plurality of search vectors. Additionally, at step 618, the final image subunit 165 determines a matching window from the plurality of search windows based on the plurality of similarity scores. Subsequently, as indicated by step 620, the final image subunit 165 generates a final image using the first image and the second image based on the template window and the matching window.

The systems and methods for pasting a plurality of images that are described hereinabove are advantageous compared to currently available systems and methods. Particularly, generating the template vector and the plurality of search vectors based on the plurality of pixels surrounding the template interest pixel and the plurality of search interest pixels advantageously reduces any errors due to X-ray dose variation between the images. Further, generating the template vector and the plurality of search vectors based on the irrelevant mask advantageously minimized errors due to implants in the subject. Also, determining a matching window amongst a plurality of search windows that span the entire search template region advantageously reduces the errors due to motion of the subject during the acquisition of the plurality of images. Consequently, the systems and methods for pasting the plurality of images that are described hereinabove lead to enhanced diagnosis of a subject.

It is to be understood that not necessarily all such objects or advantages described above may be achieved in accordance with any particular implementation. Thus, for example, those skilled in the art will recognize that the systems and techniques described herein may be embodied or carried out in a manner that achieves or optimizes one advantage or group of advantages as taught herein without necessarily achieving other objects or advantages as may be taught or suggested herein.

While the technology has been described in detail in connection with only a limited number of implementations, it should be readily understood that the invention is not limited to such disclosed implementations. Rather, the technology can be modified to incorporate any number of variations, alterations, substitutions or equivalent arrangements not heretofore described, but which are commensurate with the spirit and scope of the disclosure. Additionally, while various implementations of the technology have been described, it is to be understood that aspects of the technology may include only some of the described implementations. Accordingly, the inventions are not to be seen as limited by the foregoing description, but are only limited by the scope of the appended claims.

What is claimed is:

1. A method, comprising:
   operating an X-ray imaging device to acquire X-ray images including a first image and a second image;
   extracting a first X-ray dose associated with the first image and a second X-ray dose associated with the second image;
   calculating a dose ratio based on the first X-ray dose and the second X-ray dose;
   determining a template window in the first image and a plurality of search windows in the second image;
   generating a template vector corresponding to the template window and a plurality of search vectors corresponding to the plurality of search windows;
   calculating a plurality of similarity scores based on the template vector and the plurality of search vectors;
   determining a matching window from the plurality of search windows based on the plurality of similarity scores;
   generating a final image using the first image and the second image based on the template window and the matching window, one of the first image and the second image having been normalized based on the dose ratio, the normalized image being the one of the first image and the second image associated with a lower dose relative to the dose associated with the other of the first image and the second image; and displaying the final image on a display.

2. The method of claim 1, further comprising:
   extracting a first detector position associated with the first image and a second detector position associated with to the second image; and
   determining a template overlap region in the first image and a search overlap region in the second image based on the first detector position and the second detector position.

3. The method of claim 2, wherein determining the template window in the first image comprises:
   calculating an edge content of the template overlap region; and
   determining the template window in the template overlap region based on the edge content.

4. The method of claim 1, wherein generating the template vector corresponding to the template window comprises:
   identifying a template interest pixel in the template window; and
   generating the template vector based on the template interest pixel and one or more pixels surrounding the template interest pixel.

5. The method of claim 4, wherein generating the template vector corresponding to the template window further comprises:
   receiving an irrelevant mask of the first image; and
   generating the template vector based on the template interest pixel, the one or more pixels surrounding the template interest pixel, and the irrelevant mask.

6. The method of claim 1, wherein generating the plurality of search vectors corresponding to the plurality of search windows comprises:
   identifying a search interest pixel in each of the plurality of search windows based on a location of the template interest pixel within the template window; and
   generating the plurality of search vectors based on the plurality of search interest pixels and one or more pixels surrounding each of the plurality of search interest pixel.

7. The method of claim 1, wherein calculating the plurality of similarity scores comprises:
   determining a match number and mismatch number between the template vector and each of the plurality of search vectors; and
   calculating the plurality of search vectors based on the plurality of match numbers and the plurality of mismatch numbers.

8. A controller, comprising:
   at least one processor;
   a communication subunit executable by the at least one processor, wherein the communication subunit is configured to receive X-ray images including a first image and a second image generated by an X-ray imaging device;
   a normalizing subunit executable by the at least one processor, wherein the normalizing subunit is communicatively coupled with the communication subunit and is configured to extract a first X-ray dose associated with the first image and a second X-ray dose associated with the second image, calculate a dose ratio based on the first X-ray dose and the second X-ray dose, and normalize at least one of the first image and the second image based on the dose ratio;

a vector subunit executable by the at least one processor, wherein the vector subunit is communicatively coupled with the communication subunit and is configured to determine a template window in the first image and a plurality of search windows in the second image and generate a template vector corresponding to the template window and a plurality of search vectors corresponding to the plurality of search windows;

a comparison subunit executable by the at least one processor, wherein the comparison subunit is communicatively coupled with the vector subunit and is configured to calculate a plurality of similarity scores based on the template vector and the plurality of search vectors;

a final image subunit executable by the at least one processor, wherein the final image subunit is communicatively coupled with the comparison subunit and is configured to determine a matching window from the plurality of search windows based on the plurality of similarity scores and generate a final image using the first image and the second image based on the template window and the matching window, at least one of the first image and the second image having been normalized based on the dose ratio; and a display to display the final image.

9. A system, comprising:

an X-ray imaging device configured to generate X-ray images including a first image and a second image of a subject;

a controller communicatively coupled to the X-ray device, wherein the device controller comprises:

at least one processor;

a communication subunit executable by the at least one processor, wherein the communication subunit is configured to receive the first image and the second image from X-ray device;

a normalizing subunit executable by the at least one processor, wherein the normalizing subunit is communicatively coupled with the communication subunit and is configured to extract a first X-ray dose associated with the first image and a second X-ray dose associated with the second image, calculate a dose ratio based on the first X-ray dose and the second X-ray dose, and normalize at least one of the first image and the second image based on the dose ratio;

a vector subunit executable by the at least one processor, wherein the vector subunit is communicatively coupled with the communication subunit and is configured to determine a template window in the first image and a plurality of search windows in the second image and generate a template vector corresponding to the template window and a plurality of search vectors corresponding to the plurality of search windows;

a comparison subunit executable by the at least one processor, wherein the comparison subunit is communicatively coupled with the vector subunit and is configured to calculate a plurality of similarity scores based on the template vector and the plurality of search vectors and determine a matching window from the plurality of search windows based on the plurality of similarity scores;

a final image subunit executable by the at least one processor, wherein the final image subunit is communicatively coupled with the comparison subunit and is configured to generate a final image using the first image and the second image based on the template window and the matching window, at least one of the first image and the second image having been normalized based on the dose ratio; and a display to display the final image.

* * * * *